(12) United States Patent
Dewaegenaere

(10) Patent No.: US 9,237,853 B2
(45) Date of Patent: Jan. 19, 2016

(54) SYSTEM FOR DETECTION AND TREATMENT OF INFECTION OR INFLAMMATION

(75) Inventor: Levi Emmerik A. Dewaegenaere, s'Gravenwezel (BE)

(73) Assignee: ThermoMend International Ltd., Cybercity (MU)

(*) Notice: Subject to any disclaimer, the term of this patent is extended or adjusted under 35 U.S.C. 154(b) by 199 days.

(21) Appl. No.: 13/261,116

(22) PCT Filed: Jul. 1, 2010

(86) PCT No.: PCT/EP2010/059377
§ 371 (c)(1),
(2), (4) Date: Jan. 3, 2012

(87) PCT Pub. No.: WO2011/000918
PCT Pub. Date: Jan. 6, 2011

(65) Prior Publication Data
US 2012/0101403 A1    Apr. 26, 2012

(30) Foreign Application Priority Data

Jul. 3, 2009   (EP) .................................... 09164535
Oct. 13, 2009  (EP) .................................... 09172914

(51) Int. Cl.
*A61B 5/00*    (2006.01)
*A61B 5/01*    (2006.01)
(Continued)

(52) U.S. Cl.
CPC . *A61B 5/015* (2013.01); *A61F 7/10* (2013.01); *A61F 2007/0056* (2013.01); *A61F 2007/0075* (2013.01); *A61F 2007/0095* (2013.01)

(58) Field of Classification Search
CPC ......... A61B 5/01; A61B 5/015; G01K 13/002
USPC ......... 374/100, 101, 102, 107, 137, 141, 145; 600/549
See application file for complete search history.

(56) References Cited

U.S. PATENT DOCUMENTS 4,548,212 A   10/1985  Leung ........................... 128/736
5,662,695 A    9/1997  Mason et al.
(Continued)

FOREIGN PATENT DOCUMENTS

CN    1399532    2/2003
CN    1460008    12/2003
(Continued)

OTHER PUBLICATIONS

International Search Report and Written Opinion for International (PCT) Patent Application No. PCT/EP10/59372 mailed Sep. 24, 2010, 7 pages.
(Continued)

*Primary Examiner* — Sean Dougherty
*Assistant Examiner* — Daniel Cerioni
(74) *Attorney, Agent, or Firm* — Sheridan Ross P.C.

(57) ABSTRACT

A system for visualizing a medical treatment of a human or animal body part. The system has means for thermal treatment of the body part, means for determining the temperature distribution on the body part, and means for identifying the location of a particular temperature determined on the body part. Further, a method for visualizing the temperature characteristics of a human or animal body part is provided. The method includes the steps of comparing a first temperature distribution data set of the surface of the body part with a second temperature distribution data set of the surface of the body part, wherein the first temperature distribution data set is determined before and the second temperature distribution data set is determined after a thermal treatment of the body part, and visualizing the temperature distribution data sets of the body part.

15 Claims, 6 Drawing Sheets

(51) Int. Cl.
  *A61F 7/10* (2006.01)
  *A61F 7/00* (2006.01)

(56) References Cited

U.S. PATENT DOCUMENTS

| | | | |
|---|---|---|---|
| 5,755,755 A | 5/1998 | Panyard | |
| 5,995,868 A | 11/1999 | Dorfmeister et al. | |
| 6,017,337 A | 1/2000 | Pira | |
| 6,176,869 B1 | 1/2001 | Mason et al. | |
| 6,349,412 B1 | 2/2002 | Dean | |
| 6,763,671 B1 | 7/2004 | Klett et al. | |
| 6,893,453 B2 | 5/2005 | Agarwal et al. | |
| 7,914,563 B2 | 3/2011 | Mason et al. | |
| 2002/0026226 A1 | 2/2002 | Ein | |
| 2002/0096311 A1 | 7/2002 | Kushnir et al. | |
| 2003/0019476 A1 | 1/2003 | Chambers | |
| 2004/0019269 A1* | 1/2004 | Schaefer et al. | 600/407 |
| 2005/0103353 A1 | 5/2005 | Grahn et al. | |
| 2007/0068651 A1 | 3/2007 | Gammons et al. | |
| 2007/0185553 A1 | 8/2007 | Kennedy | |
| 2009/0018626 A1* | 1/2009 | Levinson et al. | 607/96 |
| 2009/0026471 A1 | 1/2009 | Wu et al. | |
| 2009/0118684 A1 | 5/2009 | Da Silva et al. | |
| 2009/0131835 A1 | 5/2009 | Voorhees et al. | |
| 2009/0326381 A1* | 12/2009 | Yuan et al. | 600/473 |
| 2010/0069758 A1* | 3/2010 | Barnes et al. | 600/473 |
| 2010/0234737 A1* | 9/2010 | Farage | 600/473 |
| 2011/0046472 A1* | 2/2011 | Schmidt et al. | 600/411 |
| 2011/0087096 A1* | 4/2011 | Behar | 600/438 |
| 2012/0172955 A1 | 7/2012 | Dewaegenaere | |
| 2012/0172956 A1 | 7/2012 | Dewaegenaere | |
| 2012/0172957 A1 | 7/2012 | Dewaegenaere | |
| 2012/0179231 A1 | 7/2012 | Dewaegenaere | |

FOREIGN PATENT DOCUMENTS

| | | | |
|---|---|---|---|
| CN | 1541628 | 11/2004 | |
| CN | 1741777 | 3/2006 | |
| CN | 2933354 | 8/2007 | |
| CN | 101132749 | 2/2008 | |
| CN | 101261026 | 9/2008 | |
| CN | 201129894 | 10/2008 | |
| CN | 201135537 | 10/2008 | |
| DE | 29716336 | 12/1997 | |
| DE | 20019614 U1 | 1/2001 | A61F 7/00 |
| EP | 0033528 | 8/1981 | |
| JP | S52-94697 | 8/1977 | |
| JP | 2003-126213 | 5/2003 | |
| WO | WO 01/62193 | 8/2001 | |
| WO | WO 03/000079 | 1/2003 | |
| WO | WO 2009/026471 | 2/2009 | |
| WO | WO 2009/065138 | 5/2009 | |

OTHER PUBLICATIONS

Official Action (English translation) for Chinese Patent Application No. 201080037655.6 mailed Sep. 13, 2013, 9 pages.
Extended European Search Report for European Patent Application No. 09172913.7 dated Apr. 14, 2010, 5 pages.
International Search Report and Written Opinion for International (PCT) Patent Application No. PCT/EP2010/059374 mailed Oct. 5, 2010, 10 pages.
International Preliminary Report on Patentability for International (PCT) Patent Application No. PCT/EP2010/059374 mailed Jan. 12, 2012, 8 pages.
Official Action (with English translation) for Chinese Patent Application No. 201080037662.6 mailed Jan. 3, 2014, 20 pages.
Extended European Search Report for European Patent Application No. 09172906.1 dated Oct. 5, 2010, 7 pages.
International Search Report and Written Opinion for International (PCT) Patent Application No. PCT/EP2010/059377 mailed Sep. 30, 2010, 12 pages.
Official Action (English translation) for Chinese Patent Application No. 201080037612.8 mailed Oct. 15, 2013, 6 pages.
Extended European Search Report for European Patent Application No. 09172914.5 dated Oct. 6, 2010, 7 pages.
International Search Report and Written Opinion for International (PCT) Patent Application No. PCT/EP2010/059379 mailed Sep. 24, 2010, 10 pages.
Official Action (with English translation) for Chinese Patent Application No. 201080037608.1 mailed Sep. 4, 2013, 19 pages.
Extended European Search Report for European Patent Application No. 09172912.9 dated May 6, 2010, 6 pages.
Written Opinion for International Patent Application No. PCT/EP10/59380, mailed Jun. 10, 2010, 4 pages.
International Preliminary Report on Patentability for International Patent Application No. PCT/EP10/59380, mailed Jan. 4, 2012, 5 pages.
Official Action (English translation) for Chinese Patent Application No. 201080037613.2, mailed Sep. 16, 2013, 7 pages.
Extended European Search Report for European Patent Application No. 09172908.7 dated Oct. 6, 2010, 6 pages.
Official Action (English translation) for Chinese Patent Application No. 201080037655.6 mailed Apr. 18, 2014, 10 pages.
Official Action (English translation) for Chinese Patent Application No. 201080037608.1 mailed Apr. 24, 2014, 5 pages.
International Preliminary Report on Patentability for International (PCT) Patent Application No. PCT/EP2010/059372 mailed Jan. 12, 2012, 6 pages.
International Preliminary Report on Patentability for International (PCT) Patent Application No. PCT/EP2010/059377 mailed Jan. 12, 2012, 9 pages.
International Preliminary Report on Patentability for International (PCT) Patent Application No. PCT/EP2010/059379 mailed Jan. 12, 2012, 8 pages.
International Search Report for International Patent Application No. PCT/EP2010/059380, mailed Oct. 6, 2010, 4 pages.
Official Action with English Translation for China Patent Application No. 201080037612.8, dated May 27, 2014 10 pages.
Official Action (with English translation) for Chinese Patent Application No. 201080037655.6 mailed Sep. 25, 2014, 10 pages.
Official Action (with English translation) for Russian Patent Application No. 2012103553/14 dated Oct. 28, 2014, 5 pages.
Official Action (with English translation) for Chinese Patent Application No. 201080037608.1 mailed Nov. 15, 2014, 5 pages.
Official Action (English translation) for Chinese Patent Application No. 201080037662.6 mailed Aug. 15, 2014, 5 pages.
Official Action (English translation) for Chinese Patent Application No. 201080037613.2, dated Sep. 2, 2014, 7 pages.

* cited by examiner

SYSTEM FOR DETECTION AND TREATMENT OF INFECTION OR INFLAMMATION

This Patent Application is a US National Phase Patent Application from PCT Application No. PCT/EP2010/059377, filed Jul. 1, 2010 and claiming priority from European Patent Application Nos. 09164535.8, filed Jul. 3, 2009 and 09172914.5, filed Oct. 13, 2009.

The invention relates to a system and method for visualizing temperature distributions of a human or animal body part. Further, the system and method compare data sets obtained before and after a thermal treatment of the body part and allow the determination of a diagnosis.

FIELD OF THE INVENTION

The present invention is in the technical field of therapeutic diagnosis and treatment of human or animal body.

More particularly, the present invention is in the technical field of therapeutic diagnosis and treatment of human or animal body by means of and after measuring the surface temperature of the skin before and after extracting thermal energy, in order to determine where an infection or inflammation is localized.

BACKGROUND OF THE INVENTION

Known symptoms of infections are pain, redness, swelling and temperature increase of the infected or inflamed part of the body. Despite the local nature of the infection, the symptoms regularly do not occur sufficiently localized to provide localized treatment. Especially when the infection is internal and not on or close to the skin, the symptoms may not reveal the precise location of the core of the infection. Known treatments may have to treat too large an area to be effective, or otherwise cause negative side-effects due to the larger treatment area.

Infrared visualization techniques reveal the temperature increase resulting from the infection but under the circumstances described, the temperature visualization will yield a larger area and not reveal the actual core of the infection.

In order to determine the correct diagnosis of an infection or inflammation, local thermal treatment is preferred over treatments that impact a larger part of the body than only the affected part. The optimal treatment entails the fastest and most effective result to the infected body part, with the least side-effects to the patient.

There is a need for an invention which can determine where an infection or inflammation can be localized with greater certainty in a human or animal body.

OBJECTS OF THE INVENTION

It is an object of the present invention to provide a means for localizing an infection or inflammation with increased certainty in a human or animal body.

It is a further object of the present invention to minimize side-effects caused by the application of thermal treatment to un-affected areas of a patient.

It is a further object of the present invention to create a better visualization of an infection or inflammation in a human or animal body.

It is a further object of the present invention to allow the diagnosis between infection and inflammation in a human or animal body.

Further objects and advantages of the present invention will be disclosed and become apparent from the following description.

SUMMARY OF THE INVENTION

The present invention relates to a system for visualizing a medical treatment of a human or animal body part and a method for visualizing temperature distribution data sets are provided. More specific features for preferred embodiments are set out in the dependent claims.

The present invention uses, for example, data sets obtained before and data sets obtained after a thermal treatment, e.g. a cooling, of an affected area (or any other body part), for example, in order to locate an area of infection or inflammation in a patient.

According to the present invention, a system for visualizing a medical treatment of a human or animal body part is provided. The system comprises means for thermal treatment of the body part, means for determining the temperature distribution on the body part, and means for identifying the location of a particular temperature determined on the body part.

A particular temperature may be a temperature value pre-determined by a threshold set before the thermal treatment. Further, a particular temperature may be a temperature value being an extremum of the temperature distribution (data set) determined. For example, the temperature distribution determined may be calibrated by comparing it to the pre-determined temperature values or by recognizing that the temperature determined is an extremum of the temperature distribution (data set). For example, in these cases the determined temperature is a particular temperature determined on the body part.

In a particular embodiment, the system further comprises means for visualizing the temperature distribution dependent on the location on the body part.

In a particular embodiment, the display means is adapted to provide a temperature map signature over the time of thermal treatment.

In a particular embodiment, the system further comprises means for generating a treatment protocol.

In a particular embodiment, the means for generating a treatment protocol is adapted to generate the protocol on the basis of the temperature distribution determined.

In a particular embodiment, the means for thermal treatment of the body part is a patch having fluid communication channels providing the thermal treatment.

In a particular embodiment, a sensor may be provided and may be adapted to determine the body part related parameter(s), such as the skin conductivity, the skin color, the skin temperature, the skin texture, the heart rate, the blood pressure, the blood saturation.

Additionally the system may comprise means for a controlled supply of medication, e.g., a certain pharmaceutical supplied by a drug pump, to the patient, wherein the system determines—via suitable sensors, for example, the sensor discussed above—the patient's response on the medication, namely the change of the body part related parameter(s). The system may provide a certain diagnosis based on the patient's response and/or modify the thermal treatment in a controlled manner in order to optimize the patient's treatment by means of a closed loop (feedback) control.

For example, the combination of treatment by the thermal treatment device in conjunction with other medical treatments, such as, but not limited to antibiotics, anti-inflammatory drugs, and chemotherapy drugs, can cause a positive synergistic treatment effect. In one embodiment, the thermal treatment device may by used to apply cryo-treatment to an area of the body (e.g, the arm) which is infected with a bacteria which is, for example, normally resistant to antibiotics (e.g. methicillin-resistant *Staphylococcus aureus*). The application of cryo-treatment in this way may cause a reduction in bacterial division and/or spread in the tissue, providing more time for the antibiotics to work effectively in the affected area. This may result in a favorable treatment outcome where amputation may have been the only other viable option.

Further, the invention disclosed herein could operate to monitor the patient's progress with regards to cryo-treatment in combination with other medical treatments and update the treatment protocol accordingly, for example, the choice of medicine and optimal dose rate to maximize pharmaceutical efficacy.

For example, the temperature distribution data may be obtained by an IR (infrared) camera and may be displayed to the physician and/or used for feedback control of the thermal treatment. Furthermore, the time lapsed during the thermal treatment may also be taken into account when controlling the thermal treatment based on the determination of the various body part related parameter(s).

While the present invention discusses the use of biofeedback to adapt a treatment protocol, it is advantageous to disclose the optimal means of obtaining a biofeedback reading, which are preferably non-invasive. For example, the amount of thermal exchange between the thermal pad or Peltier thermal exchange element and skin can be determined by using a temperature sensitive surface between such thermal pad or Peltier thermal exchange element and skin. Alternatively, a measurement of power output to the fluid in the thermal pad or the Peltier thermal exchange element itself can provide an indirect determination of thermal exchange with a body. Alternatively, the amount of thermal exchange between a Peltier thermal exchange element and the skin (such Peltier thermal exchange element preferably being constructed in the manned disclosed in U.S. Pat. No. 6,017,337 by Pira) can be determined indirectly by measuring temperature difference between the cold side and hot side of the Peltier element, and the rate of flow of liquid cooling the heat sink on the hot side. Alternatively, a direct measurement of biofeedback (e.g. temperature) from a patient can be obtained by using sensor means to obtain a reading from a drainage catheter, which, for example, has been inserted into the body following knee reconstructive surgery. Although various preferred means of obtaining biofeedback readings have been disclosed herein, other means of obtaining such readings are not excluded.

In a particular embodiment, the means for thermal treatment of the body part is a patch having a Peltier element providing the thermal treatment.

The Peltier effect uses a thermoelectric cooling to create a heat flux between the junction of two different types of materials. A Peltier cooler, heater, or thermoelectric heat pump is a solid-state active heat-pump which transfers heat from one side of the device to the other side against the temperature gradient (from cold to hot), with consumption of electrical energy.

According to the present invention, a method for visualizing the temperature characteristics of a human or animal body part is provided. The method comprises the steps of comparing a first temperature distribution data set of the surface of the body part with a second temperature distribution data set of the surface of the body part, wherein the first temperature distribution data set is determined before and the second temperature distribution data set is determined after a thermal treatment of the body part, and visualizing the temperature distribution data sets of the body part.

In a particular embodiment, the visualizing step comprises a visual identification of the location of a particular temperature of the first and/or second temperature distribution data set.

In a particular embodiment, the comparing step further comprises providing a temperature map signature on the basis of multiple temperature distribution data sets obtained during the thermal treatment of the body part.

In a particular embodiment, the method further comprises the step of determining a diagnosis of the disease on the basis of the comparing of the data sets.

In a particular embodiment, the determination of the diagnosis is carried out by calibrating the data sets dependent on known characteristic data sets.

Known characteristic data sets are data sets which were obtained before carrying out the thermal treatment and before obtaining the temperature distribution data sets as discussed above. For example, the known characteristic data sets may be data sets from a database of data obtained from former patients and their thermal treatments. Further, the data sets may be data obtained from theoretical simulations carried out by a computer for the particular disease.

In a particular embodiment, the method further comprises the step of generating a treatment protocol on the basis of the comparing of the data sets.

In a particular embodiment, the treatment protocol is amended on the basis of the comparing of the data sets.

According to the present invention, a computer program product is provided. The computer program product comprises one or more computer readable media having computer executable instructions for actuating and controlling the steps of the method as discussed above.

DETAILED DESCRIPTION OF THE INVENTION

Figure 1:
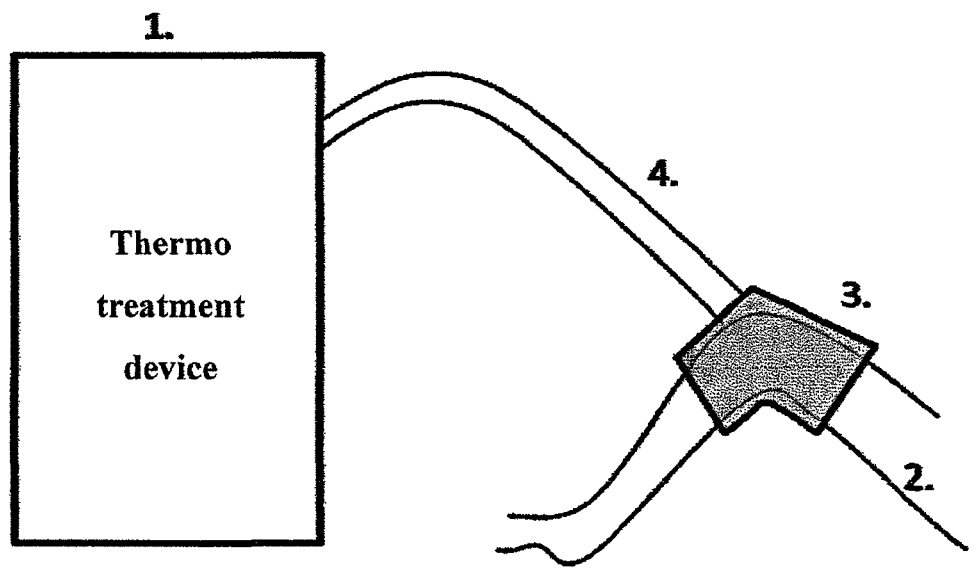
FIG. 1 schematically shows the general concept for obtaining temperature distribution data sets.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. In addition, an aspect described in conjunction with a particular embodiment of the present invention is not necessarily limited to that embodiment and can be practiced in any other embodiments of the present invention.

In one embodiment, the present invention combines cooling as a pre-treatment with infrared visualization in order to obtain a more precise location of the core of the infection.

In FIG. 1 a thermal treatment device (1) is used to cool part of the body suspected to contain the affected area of inflammation or infection (2). The heat exchange is carried out through an energy exchange device (3). One embodiment of this energy exchange device is a patch through which a cooling liquid flows, such cooling liquid being supplied by the thermo-treatment device through a hydraulic conduit (4). In another embodiment, the cooling is generated at the energy exchange device (3) itself, e.g. through Peltier elements embedded in the energy exchange device. In this example, the conduit (4) is an electric conduit.

Figure 2:
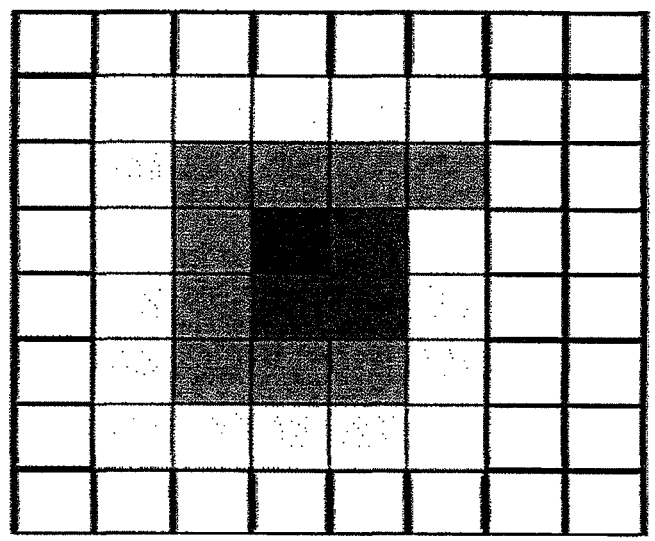
FIG. 2 is a graphical representation of a localized infection or inflammation.

After applying controlled cooling to the larger area where the infection symptoms manifest, an infrared visualization device may monitor the body part and generates an image as depicted, for example, in FIG. 2. This image reveals the core of the infection and may be effectively as a localized area. Alternatively, some other means of obtaining a temperature reading from the skin can be used instead of an infrared visualization device, for example, but not limited to, a temperature sensitive pad or layer. The pinpointed area can then be identified and visual markers can be applied (e.g. marking a point or a small area on the skin). Subsequently, the following treatment can be applied to the pinpointed areas only.

Advantageously, this allows the fastest and most effective treatment, while minimizing unwanted side effects.

In an alternative embodiment the system can be used to detect whether the affected body part is subject to inflammation or infection. This is because the infrared visualization device will generate an alternative image or heat map 'signature' over the period of cooling, for an infection as opposed to inflammation. This 'signature' can be generated by mapping a function of the rate of cooling in the body part image against time. For example, an infection will cool at a slower rate versus time than inflammation. Therefore, the system can be used to obtain diagnostic information, and such information can be used to generate a treatment protocol for a patient, or amend an existing treatment protocol.

Figure 3:
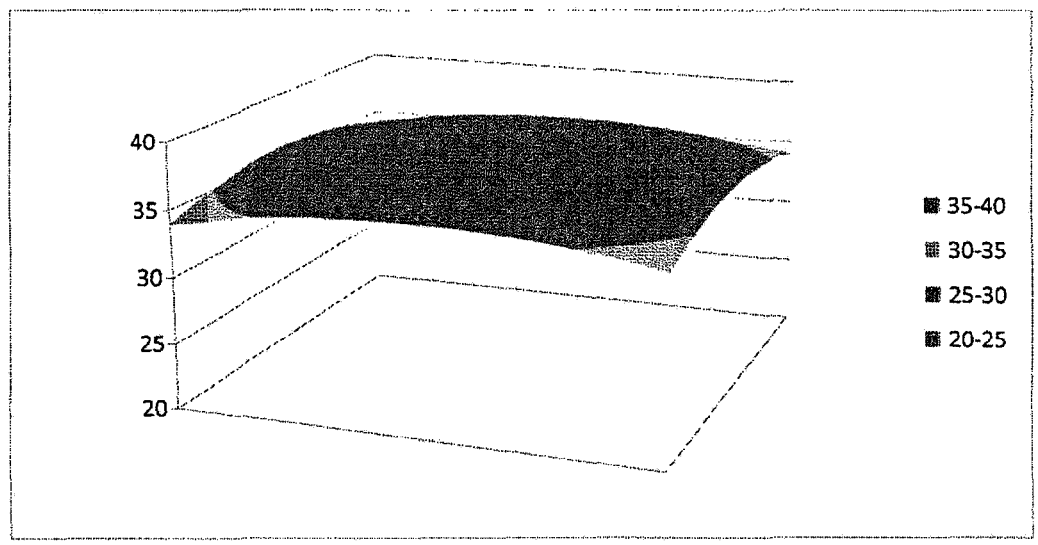
FIGS. 3-7 show thermal pattern of tissue at subsequent instances in time.
Figure 3:
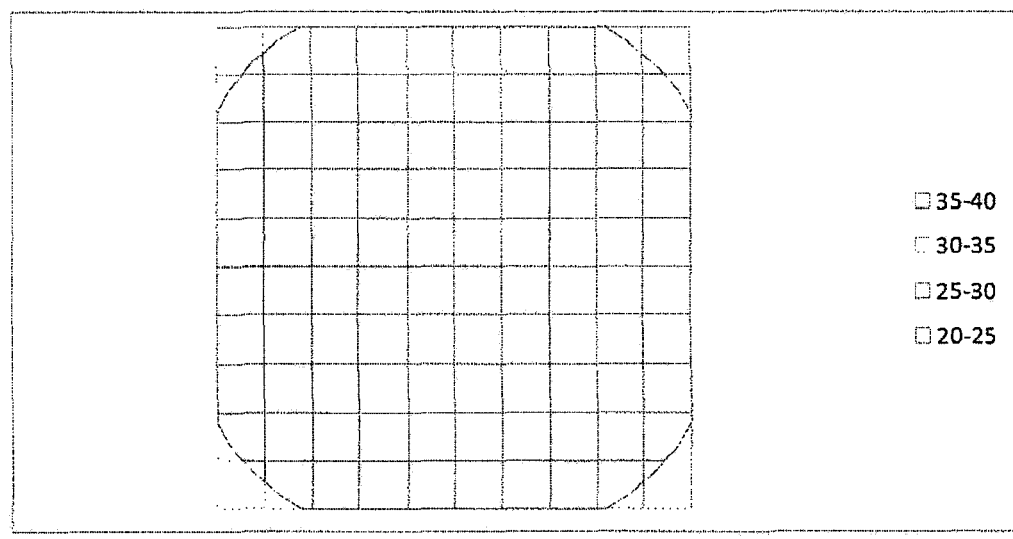
Figure 4:
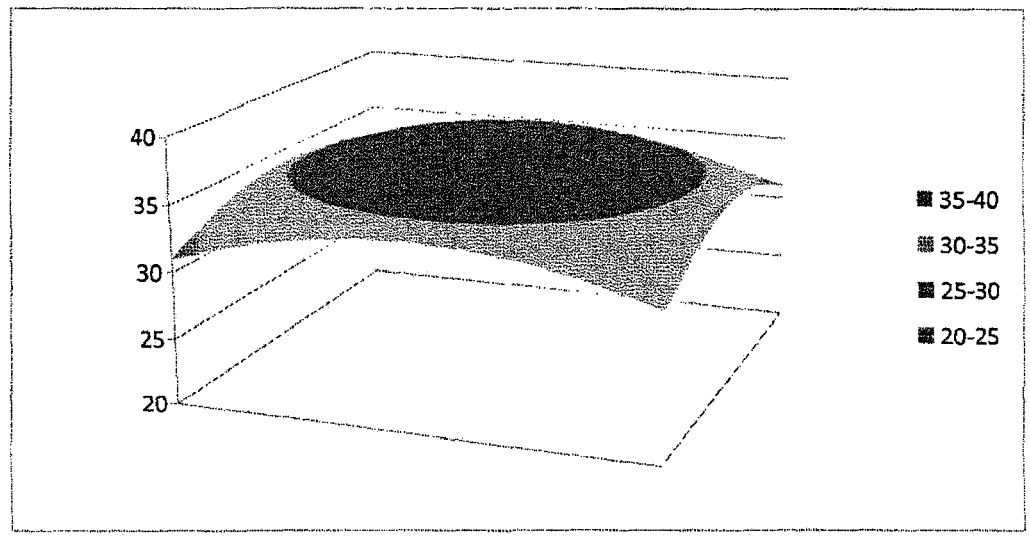
Figure 4:
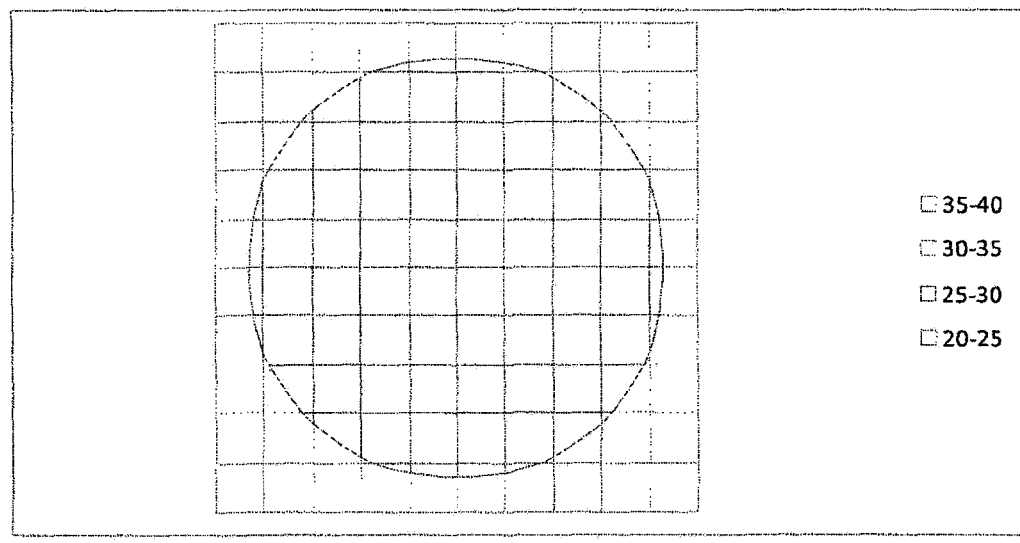
Figure 5:
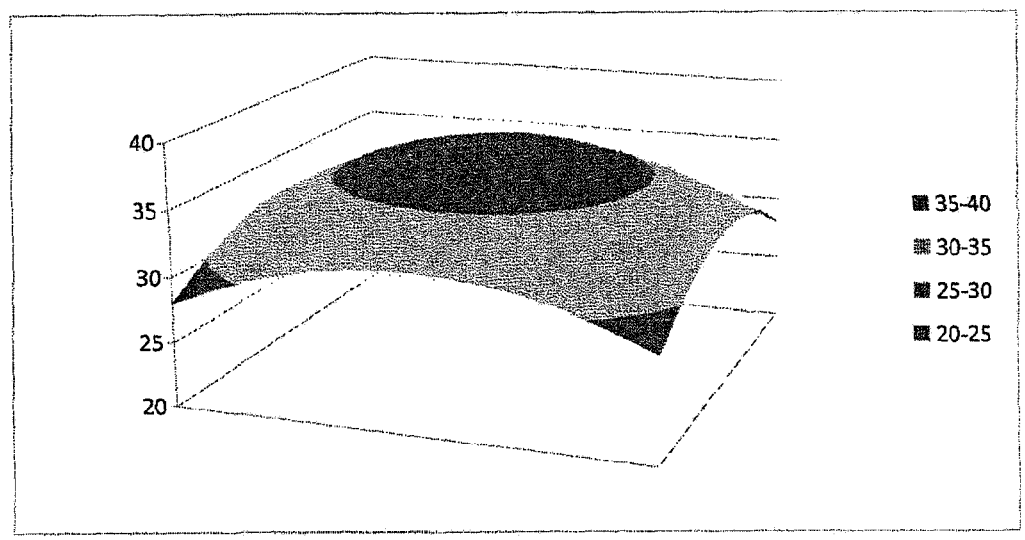
Figure 5:
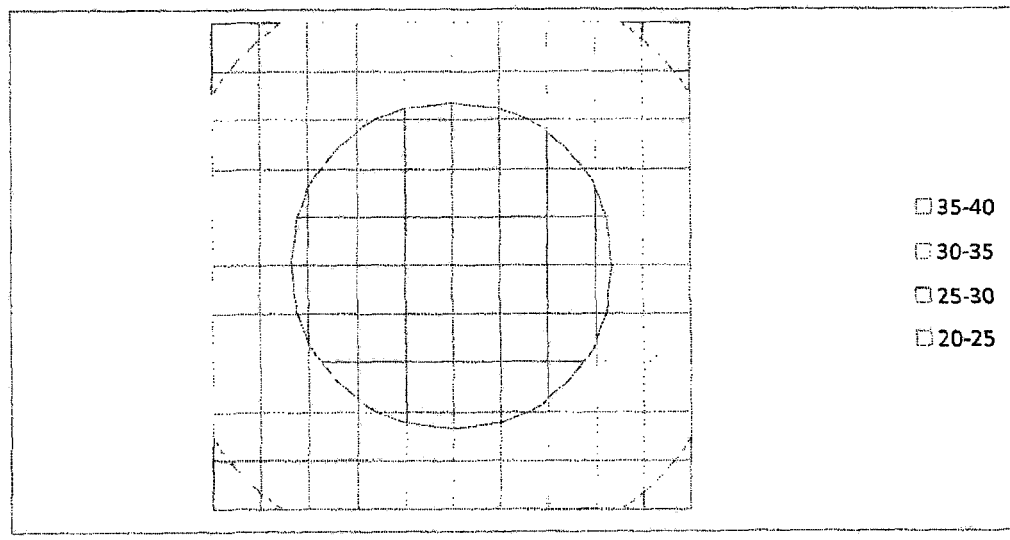
Figure 6:
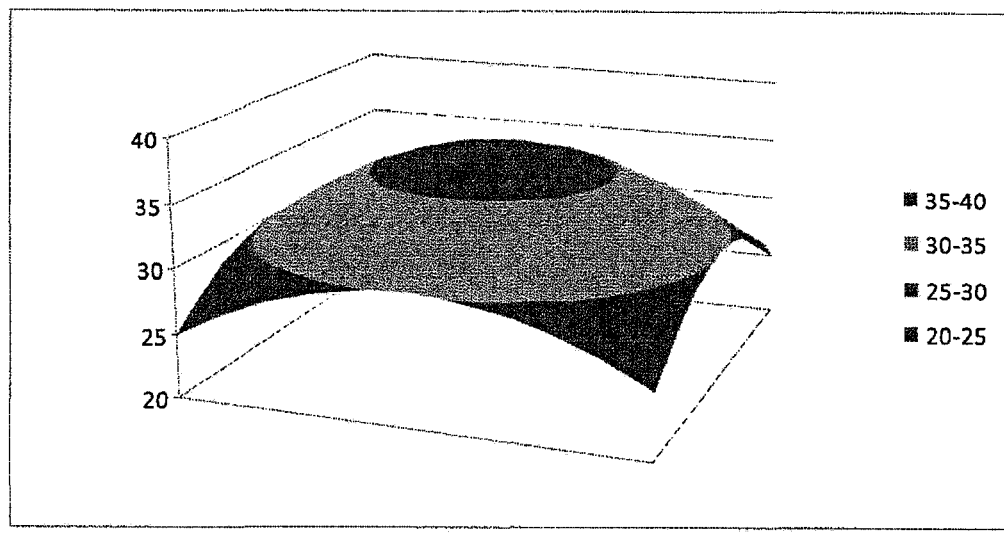
Figure 6:
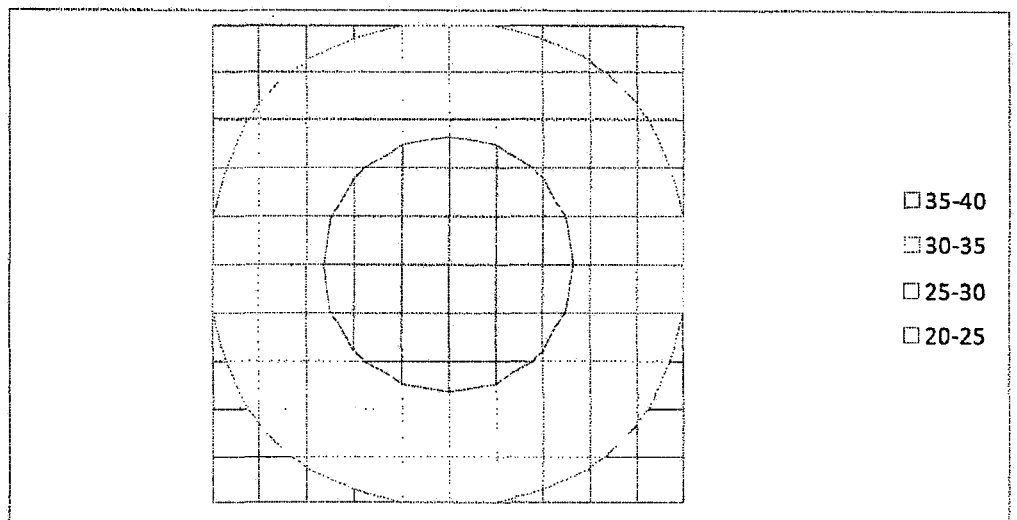
Figure 7:
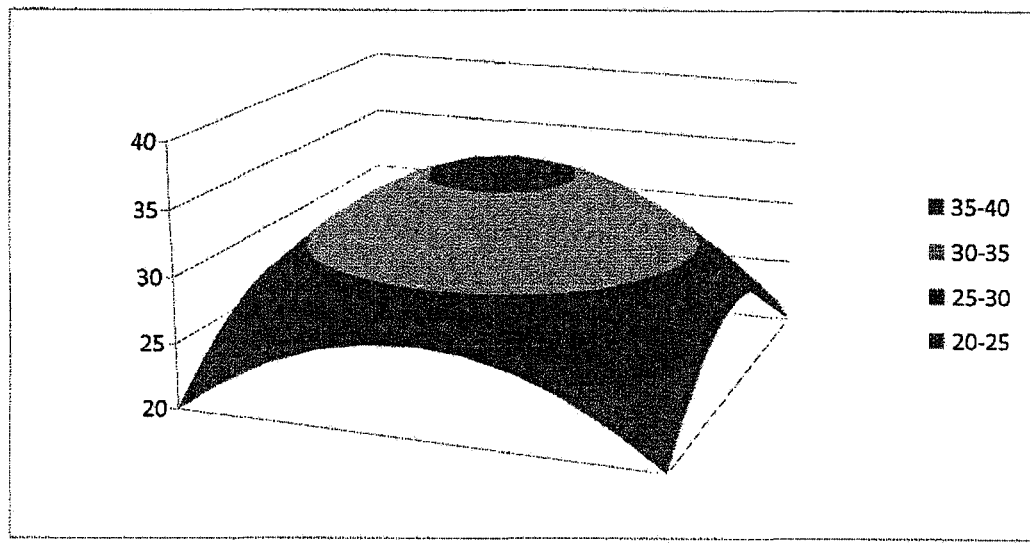
Figure 7:
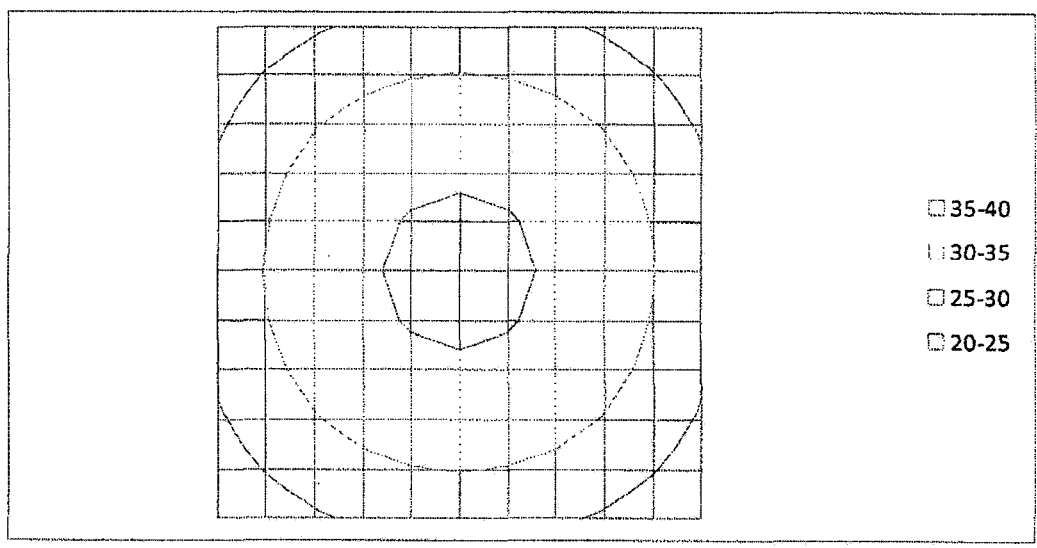

As the preferred embodiment of generating said heat map 'signature' FIGS. 3-7 display on the vertical axis a series a thermal pattern of tissue taken at subsequent instances in time. The two images in FIG. 3 are taken before the cooling treatment, the images of FIG. 7 are taken at the end of the treatment. The (optional) pictures of FIGS. 4-6 are taken chronologically during the cooling treatment.

All pictures at the top of FIGS. 3-7 contain a 3D representation, where the vertical axis represents the temperature and the horizontal axes represent special coordinates. In the images at the bottom of FIGS. 3-7, both axes represent special coordinates and the contours represent equi-temperature lines.

FIG. 3 shows a large area of elevated temperature. As the area is large, it is not possible to pinpoint the location of the inflammation. As the tissue is cooled, different parts of the thermal picture cool down at different speeds. At the end of the treatment the inflammation is easy to pinpoint.

The rate and profile of temperature decline is called the "thermal space-time signature". For example, thresholds may be applied to the thermal signature to conclude on the specific location of the inflammation.

The thresholds include (but are not limited to) (1) rates of temperature decline at a specific point in space, (2) decline of size of equi-temperature contours during a given amount of time and (3) temperature differential at a specific point in space over a given amount of time.

While the invention has been illustrated and described in detail in the foregoing description, such illustration and description are to be considered illustrative or exemplary and non-restrictive; the invention is thus not limited to the disclosed embodiments. Features mentioned in connection with one embodiment described herein may also be advantageous as features of another embodiment described herein without explicitly showing these features. Variations to the disclosed embodiments can be understood and effected by those skilled in the art and practicing the claimed invention, from a study of the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures can not be used to advantage.

The invention claimed is:

1. A system for displaying a medical treatment of a human or animal body part, comprising:
   means for thermal treatment of the body part;
   means for determining a temperature distribution, the means for determining a temperature distribution being configured to obtain a first temperature distribution data set of the surface of the body part and a second temperature distribution data set of the surface of the body part, the first temperature distribution data set representing a temperature distribution of the body part before a treatment of the body part, and the second temperature distribution data set representing a temperature distribution of the body part after a treatment has begun on the body part;
   a computer programmed to:
      determine a 3-D representation of a temperature map signature over a time of thermal treatment where a vertical axis represents a temperature and a horizontal axis represents special coordinates or both axes in the 3-D representation represent special coordinates and the contours represent equi-temperature lines;
      compare the first temperature distribution data set to the second temperature distribution data set to determine a rate of change of the temperature distribution of the body part over a period of time;
      detect a specific location of the body part that is subject to a condition based on the temperature map signature and the rate of change, wherein the condition is selected from the group consisting of: inflammation or infection;
      compare the rate of change to a database to determine whether the condition is inflammation of infection, the database containing data obtained from thermal treatments of one or more former patients and data from theoretical simulations previously carried out by the computer;
      determine that the body part is subject to inflammation when the temperature map signature shows the body part cooling at a first rate and the rate of change being a first rate;
      determine that the body part is subject to infection when the temperature map signature shows the body part cooling at a second rate and the rate of change being a second rate;
      wherein the second rate is slower than the first rate; and
      generating or amending a treatment protocol based on the rate of change; and
   means for displaying the temperature distribution, wherein the means for displaying the temperature distribution is configured to display the temperature distribution dependent on the location of the body part and wherein the means for displaying the temperature distribution is configured to provide the 3D representation of the temperature map signature over the time of thermal treatment.

2. The system of claim 1, wherein the computer is adapted to generate the protocol on the basis of the temperature distribution determined.

3. The system of claim 1, wherein the means for thermal treatment of the body part is a patch having fluid communication channels providing the thermal treatment.

4. The system of claim 1, wherein the means for thermal treatment of the body part is a device having a Peltier element providing the thermal treatment.

5. A method, implemented on a system for the detection and treatment of infection or inflammation, for displaying temperature characteristics of a human or animal body part, the method comprising:
  using a thermal treatment device having an energy exchange device to perform a thermal treatment of the body part; and
  obtaining, using a camera, a first temperature distribution data set of the surface of the body part, the first temperature distribution data set representing a temperature distribution of the body part before a treatment of the body part;
  obtaining, using the camera, a second temperature distribution data set of the surface of the body part, the second temperature distribution data set representing a temperature distribution of the body part after a treatment has begun on the body part;
  implementing on a computer via a computer program product:
  determining a 3-D representation of a temperature map signature over a time of thermal treatment where a vertical axis represents a temperature and a horizontal axis represents special coordinates or both axes in the 3-D representation represent special coordinates and the contours represent equi-temperature lines;
  comparing the first temperature distribution data set to the second temperature distribution data set to determine a rate of change of the temperature distribution of the body part over a period of time;
  detecting a specific location of the body part that is subject to a condition based on the temperature map signature and the rate of change, wherein the condition is selected from the group consisting of: inflammation or infection;
  comparing the rate of change to a database to determine whether the condition is inflammation or infection, the database containing data obtained from thermal treatments of one or more former patients and data from theoretical simulations previously carried out by the computer;
  determining that the body part is subject to inflammation when the temperature map signature shows the body part cooling at a first rate and the rate of change being a first rate;
  determining that the body part is subject to infection when the temperature map signature the body part cooling at a second rate and the rate of change being a second rate; wherein the second rate is slower than the first rate; and
  generating or amending a treatment protocol based on the rate of change; and
  displaying on a display, the 3-D representation of the temperature map signature over the time of thermal treatment.

6. The method of claim 5, further comprising the steps of:
  comparing the first temperature distribution data set of the surface of the body part with the second temperature distribution data set of the surface of the body part, between the first determining step and the displaying step; and
  visualizing at least one of the first and second temperature distribution data sets.

7. The method of claim 6, further comprising the step of:
  determining a diagnosis of a disease on the basis of a comparison of the data sets.

8. The method of claim 7, wherein the determination of the diagnosis is carried out by calibrating the data sets dependent on known characteristic data sets.

9. The method of claim 8, wherein the treatment protocol is amended on the basis of a comparison of the data sets.

10. A non-transitory computer readable information storage media having stored thereon instructions, that when executed by a processor, cause to be performed a method for displaying the temperature characteristics of a human or animal body part, the method comprising:
  performing a thermal treatment of the body part using a thermal treatment device having an energy exchange device;
  obtaining, using a camera, a first temperature distribution data set of the surface of the body part, the first temperature distribution data set representing a temperature distribution of the body part before a treatment of the body part;
  obtaining, using the camera, a second temperature distribution data set of the surface of the body part, the second temperature distribution data set representing a temperature distribution of the body part after a treatment has begun on the body part;
  determining a 3-D representation of a temperature map signature over a time of thermal treatment where a vertical axis represents a temperature and a horizontal axis represents special coordinates or both axes in the 3-D representation represent special coordinates and the contours represent equi-temperature lines;
  comparing the first temperature distribution data set to the second temperature distribution data set to determine a rate of change of the temperature distribution of the body part over a period of time;
  detecting a specific location of the body part that is subject to a condition based on the temperature map signature and the rate of change, wherein the condition is selected from the group consisting of: inflammation or infection;
  comparing the rate of change to a database to determine whether the condition is inflammation or infection, the database containing data obtained from thermal treatments of one or more former patients and data from theoretical simulations previously carried out by the computer;
  determining that the body part is subject to inflammation when the temperature map signature shows the body part cooling at a first rate and the rate of change being a first rate;
  determining that the body part is subject to infection when the temperature map signature the body part cooling at a second rate and the rate of change being a second rate; wherein the second rate is slower than the first rate; and
  generating or amending a treatment protocol based on the rate of change; and
  displaying on a display, the 3-D representation of the temperature map signature over the time of thermal treatment.

11. The media of claim 9, further comprising:
  comparing the first temperature distribution data set of the surface of the body part with the second temperature distribution data set of the surface of the body part, between the first determining step and the displaying step; and
  visualizing at least one of the first and second temperature distribution data sets.

12. The media of claim 11, further comprising determining a diagnosis of a disease on the basis of the data sets.

13. The media of claim 12, wherein the determination of the diagnosis is carried out by calibrating the data sets dependent on known characteristic data sets.

14. The media of claim 12, wherein the treatment protocol is amended on the basis of a comparison of the data sets.

15. A system configured to visualize a medical treatment of a human or animal body part, comprising:
- a thermal treatment device and energy exchange device to thermally treat the body part;
- a camera configured to obtain a first temperature distribution data set of the surface of the body part and a second temperature distribution data set of the surface of the body part, the first temperature distribution data set representing a temperature distribution of the body part before a treatment of the body part, and the second temperature distribution data set representing a temperature distribution of the body part after a treatment has begun on the body part;
- a computer programmed to
  - determine a 3-D representation of a temperature map signature over a time of thermal treatment where a vertical axis represents a temperature and a horizontal axis represents special coordinates or both axes in the 3-D representation represent special coordinates and the contours represent equi-temperature lines;
  - compare the first temperature distribution data set to the second temperature distribution data set to determine a rate of change of the temperature distribution of the body part over a period of time;
  - detect a specific location of the body part that is subject to a condition based on the temperature map signature and the rate of change, wherein the condition is selected from the group consisting of: inflammation or infection;
  - compare the rate of change to a database to determine whether the condition is inflammation of infection, the database containing data obtained from thermal treatments of one or more former patients and data from theoretical simulations previously carried out by the computer;
  - determine that the body part is subject to inflammation when the temperature map signature shows the body part cooling at a first rate and the rate of change being a first rate;
  - determine that the body part is subject to infection when the temperature map signature shows the body part cooling at a second rate and the rate of change being a second rate;
- wherein the second rate is slower than the first rate; and
  - generating or amending a treatment protocol based on the rate of change; and
- a display configured to provide the 3-D representation of the temperature map signature over the time of thermal treatment.

* * * * *

UNITED STATES PATENT AND TRADEMARK OFFICE
CERTIFICATE OF CORRECTION

PATENT NO. : 9,237,853 B2  
APPLICATION NO. : 13/261116  
DATED : January 19, 2016  
INVENTOR(S) : Levi Emmerik A. Dewaegenaere Page 1 of 1

It is certified that error appears in the above-identified patent and that said Letters Patent is hereby corrected as shown below:

Claims

Claim 11, column 8, line 60, replace "claim 9" with --claim 10-- therein.

Claim 12, column 9, line 2, after "basis of" insert --a comparison-- therein.

Claim 14, column 9, line 6, replace "claim 12" with --claim 11-- therein.

Claim 15, column 9, line 21, after "programmed to" insert --:-- therein.

Signed and Sealed this  
Twenty-eighth Day of June, 2016

Michelle K. Lee  
*Director of the United States Patent and Trademark Office*